United States Patent
Guidotti et al.

(10) Patent No.: US 11,045,362 B2
(45) Date of Patent: Jun. 29, 2021

(54) DISPOSABLE ABSORBENT HYGIENE PRODUCT COMPRISING ABSORBENT ASSEMBLY

(71) Applicant: Essity Hygiene and Health Aktiebolag, Gothenburg (SE)

(72) Inventors: Edward Guidotti, Gothenburg (SE); Rikard Vilhelm Meyer Noren, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 17/040,780

(22) PCT Filed: Mar. 26, 2018

(86) PCT No.: PCT/EP2018/057657
§ 371 (c)(1),
(2) Date: Sep. 23, 2020

(87) PCT Pub. No.: WO2019/185112
PCT Pub. Date: Oct. 3, 2019

(65) Prior Publication Data
US 2021/0000662 A1 Jan. 7, 2021

(51) Int. Cl.
*A61F 13/535* (2006.01)
*A61F 13/53* (2006.01)
*A61F 13/49* (2006.01)

(52) U.S. Cl.
CPC ...... *A61F 13/535* (2013.01); *A61F 13/49007* (2013.01); *A61F 2013/5307* (2013.01); *A61F 2013/530051* (2013.01)

(58) Field of Classification Search
CPC .............. A61F 13/535; A61F 13/49007; A61F 13/532; A61F 2013/530051; A61F 2013/5307; A61F 2013/530518
See application file for complete search history.

(56) References Cited

U.S. PATENT DOCUMENTS

| | | | |
|---|---|---|---|
| 4,938,753 A | 7/1990 | Van Gompel et al. | |
| 5,550,189 A | * 8/1996 | Qin | A61L 15/28 525/54.3 |

(Continued)

FOREIGN PATENT DOCUMENTS

| | | |
|---|---|---|
| CN | 204951357 U | 1/2016 |
| EP | 0692231 A1 | 1/1996 |

(Continued)

OTHER PUBLICATIONS

International Searching Authority, Search Report and Written Opinion issued in PCT/EP2018/057657, dated Jan. 7, 2019 (11 pages).

(Continued)

*Primary Examiner* — Michele M Kidwell
(74) *Attorney, Agent, or Firm* — Wood Herron & Evans LLP

(57) ABSTRACT

A disposable absorbent hygiene product is provided, including a main part having a body facing surface intended to face the body of a user and a garment facing surface intended to face away from the body of a user. The main part includes a liquid permeable topsheet at the body facing surface, a liquid impermeable backsheet at the garment facing surface, and an absorbent assembly arranged between said topsheet and said backsheet. The absorbent assembly includes a first absorbent core and a second absorbent core arranged in a stacked relationship.

17 Claims, 3 Drawing Sheets

(56) References Cited

U.S. PATENT DOCUMENTS

| | | | | |
|---|---|---|---|---|
| 5,562,650 | A | * | 10/1996 | Everett ............ A61F 13/15203 604/378 |
| 5,938,753 | A | * | 8/1999 | Arimilli ............ G06F 13/4013 710/315 |
| 6,383,960 | B1 | * | 5/2002 | Everett ................ A61F 13/535 442/317 |
| 2006/0178650 | A1 | * | 8/2006 | Hakansson ....... A61F 13/53717 604/378 |
| 2013/0331806 | A1 | * | 12/2013 | Rosati ............... A61F 13/53743 604/366 |
| 2014/0276510 | A1 | * | 9/2014 | Ducker ................ A61F 13/531 604/365 |
| 2015/0148769 | A1 | * | 5/2015 | Johansson ............ A61F 13/535 604/385.23 |
| 2015/0328063 | A1 | * | 11/2015 | Esping Ostlin ....... A61F 13/533 604/379 |
| 2017/0135869 | A1 | | 5/2017 | Moriya et al. |
| 2021/0000661 | A1 | * | 1/2021 | Guidotti ............ A61F 13/49007 |

FOREIGN PATENT DOCUMENTS

| | | | | |
|---|---|---|---|---|
| EP | 3205318 | A1 | | 8/2017 |
| JP | 2015213651 | A | | 12/2015 |
| JP | 2017104255 | A | | 6/2017 |
| KR | 20160003263 | U | | 9/2016 |
| WO | 97/47263 | | * 12/1997 | ............ A61F 13/15 |
| WO | 2014004439 | A1 | | 1/2014 |
| WO | 2015095003 | A1 | | 6/2015 |

OTHER PUBLICATIONS

Australian Government, IP Australia, Examination Repot No. 2 issued in AU App. No. 2018415282, dated Mar. 11, 2021 (5 pages).
National Intellectual Property Administration (CNIPA) of the People's Republic of China, Office Action issued in CN App. No. 201880090590.8 dated Mar. 2, 2021 (with English Translation) 14 pages.

* cited by examiner

DISPOSABLE ABSORBENT HYGIENE PRODUCT COMPRISING ABSORBENT ASSEMBLY

CROSS-REFERENCE TO RELATED APPLICATION

This application is a national phase entry of, and claims priority to, International Application No. PCT/EP2018/057657, filed Mar. 26, 2018. The above-mentioned patent application is incorporated herein by reference in its entirety.

TECHNICAL FIELD

This application relates to a disposable absorbent hygiene product.

BACKGROUND

Disposable absorbent hygiene products, for example in the form of diapers, incontinence garments, pads, inserts and the like, are well known. Such articles are used to for absorbing, distributing and storing various types of body exudates, for example urine, while providing a high level of comfort and sense of dryness to the wearer during use. A conventional disposable absorbent product is normally designed with an absorbent core which is sandwiched between a topsheet and a backsheet.

General requirements for disposable absorbent hygiene products in the field of incontinence products is liquid handling and leakage security. As to liquid handling, it is for example important that the products are able to absorb and store liquids while allowing for the skin covered by the product to be dry, and as to leakage security, it is for example important that the risk for leakage of body exudates to the outside of the product is reduced, as such leakages would be unpleasant to the wearer and lead to soiling of underwear, beds, etc., with an increased workload on care givers as a consequence.

There is also a desire to reduce the cost and material usage for the incontinence products. Nevertheless, incontinence products for use by adults, e.g. in elderly care, need to have relatively large physical dimensions to satisfactory cover the urogenital area of the wearer and to be able to be properly fitted to the wearer.

Even though approaches taken in the prior art fulfill certain requirements related to the liquid handling and material usage, there is still a need for further improvements. To this end, it would be desirable to improve disposable absorbent hygiene products to overcome the deficiencies in the art.

SUMMARY

In order to achieve these technical objectives, there is provided a disposable absorbent hygiene product according to embodiments of the present invention.

More specifically, the disposable absorbent hygiene product includes a main part having a body facing surface intended to face the body of a user and a garment facing surface intended to face away from the body of a user, the main part comprising a liquid permeable topsheet at the body facing surface, a liquid impermeable backsheet at the garment facing surface, and an absorbent assembly arranged between the topsheet and the backsheet. The main part has a front end and a back end, and defines a longitudinal direction from the front end towards the back end and a transversal direction perpendicular to the longitudinal direction.

The absorbent assembly comprises a first absorbent core and a second absorbent core arranged in a stacked relationship.

The first absorbent core has a longitudinal length ($L_{abs}$) of from 500 to 1000 mm and a transversal width ($W_{abs}$) of from 200 to 450 mm; and comprises a mixture of cellulosic fibers and optionally super absorbent particles, with a super absorbent particle concentration of from 0 to 30 wt %, and a cellulosic fiber basis weight of from 50 to 200 g/m².

The second absorbent core (132) has a longitudinal length of from 20% to 80% of the longitudinal length ($L_{abs}$) of said first core; and comprises a mixture of cellulosic fibers and super absorbent particles, with a super absorbent particle concentration of from 20 to 70 wt %, and a cellulosic fiber basis weight of from 250 to 500 g/m².

The longitudinal ends of the second core are located between the longitudinal ends of the first core.

Further aspects, advantages and advantageous features of the application are disclosed in the following description.

BRIEF DESCRIPTION OF THE DRAWINGS

The features and advantages of the invention will be appreciated upon reference to the following drawings. The accompanying drawings, which are incorporated in and constitute a part of this specification, illustrate one or more embodiments of the invention and, together with the general description given above and the detailed description given below, explain the one or more embodiments of the invention.

DETAILED DESCRIPTION

The present disclosure relates to an absorbent assembly, a disposable absorbent hygiene product comprising such an assembly as well as a method for the manufacture of a disposable absorbent hygiene product.

Figure 1:
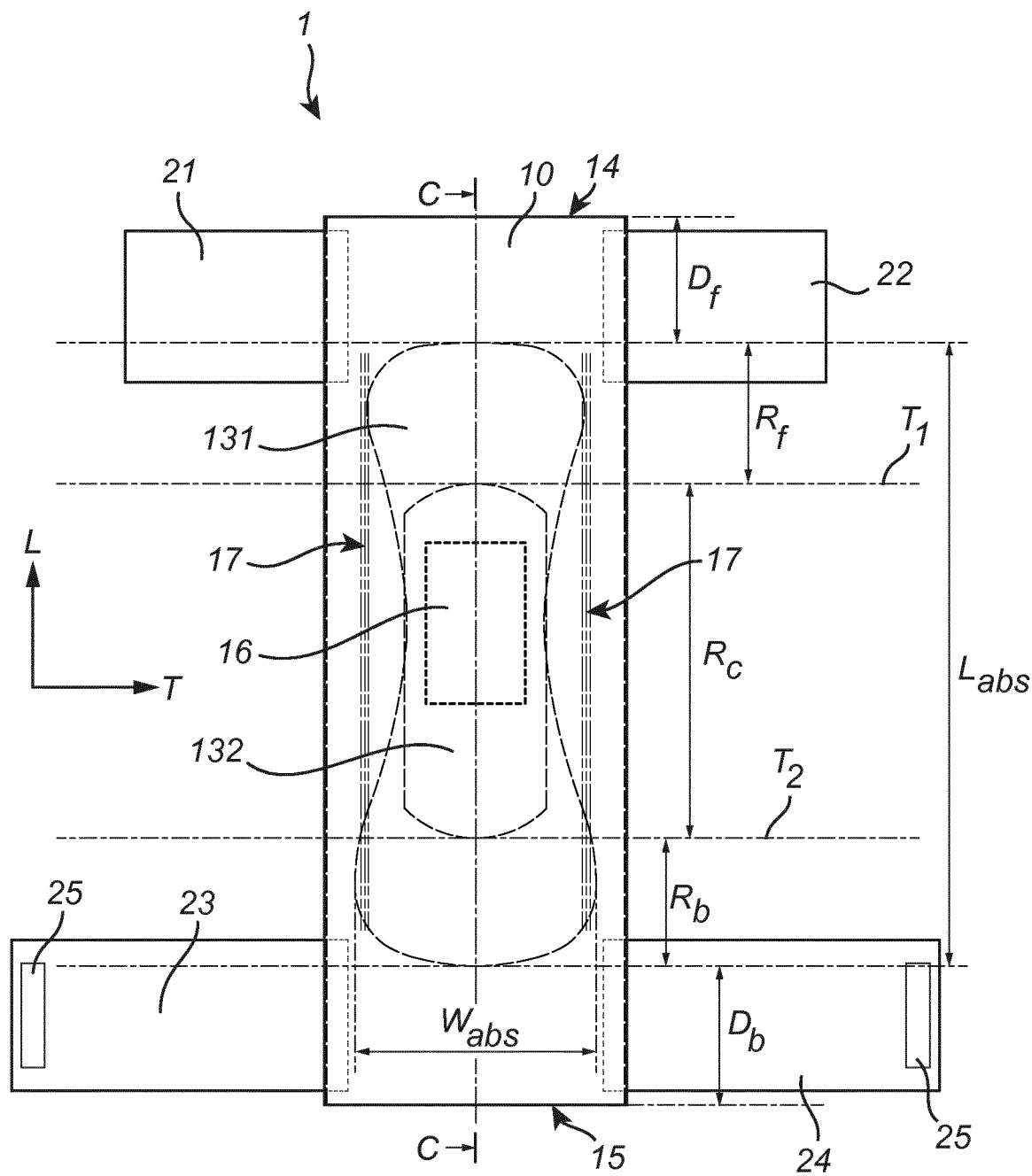
FIG. 1 is a top view of a disposable absorbent hygiene product in the form of an open-type diaper.

It is to be noted that while the disposable hygiene product in FIG. 1 is illustrated as an open diaper, the present application also relates to other types of disposable absorbent hygiene articles, such as absorbent pads, belted diapers, pant-like diapers and removable inserts.

Different embodiments of the present application will be described more fully hereinafter with reference to the enclosed drawings. The embodiments disclosed herein can, however, be realized in many different forms and should not be construed as being limited to the embodiments set forth herein.

The disposable absorbent hygiene product 1 comprises a main part 10 having a body facing surface intended to face the body of a user and a garment facing surface intended to face away from the body of a user, the main part comprising a liquid permeable topsheet 11 at the body facing surface, a liquid impermeable backsheet 12 at the garment facing surface, and an absorbent assembly 13 arranged between the topsheet and the backsheet.

In the context of the present application, "disposable" is used in its ordinary sense to mean an article that is disposed or discarded after a limited number of usage events over varying lengths of time, for example, less than about 10 events, less than about 5 events, or after 1 event.

In the disposable absorbent hygiene product illustrated in FIG. 1, the topsheet 11 and the backsheet 12 extend outside the outer contour of the absorbent assembly 13 and are joined together outside the absorbent assembly contour using methods commonly known in the art, such as gluing or welding by heat or ultrasound.

The main part 10 has a front end 14 intended to be at the front (belly) waist region of the user, and back end 15 intendent to be at the back-waist region of the user when the product is worn. The main part defines a longitudinal direction L from the front edge/end towards the back edge/end, as well as a transversal direction T perpendicular to the longitudinal direction.

Longitudinal side edges connect the front edge and the back edge of the main portion on mutually opposite sides of an imaginary longitudinal centerline C.

A pair of front side panels 21, 22 may each be attached to the main part 10 at the longitudinal side edges at or close to the front end thereof. A pair of rear side panels 23, 24 may also be attached to the main part 10 at the longitudinal side edges close to the rear end thereof.

The rear side panels 23, 24 may be provided with fastening means intended to be fastened on the garment facing surface of the corresponding front side panels 21, 22 or on the garment facing surface of the main part 10 in order to fit the disposable absorbent hygiene product around the waist of a wearer. The fastening means 25 may for example be mechanical fasteners, such as hooks, or pressure sensitive adhesive.

Elastic means 17 that extends in a generally longitudinal manner may be attached to the main part 10, such as sandwiched between the topsheet and the backsheet close to the longitudinal side edges for providing leg cuffs, as is commonly known in the art. Such elastic means may comprise one or more elastic threads, elastic film strips or elastic foam strips, and may be attached to the main part 10 in a stretched state in order to exert a longitudinally contracting force on the disposable absorbent hygiene product 1.

Topsheet

A liquid permeable topsheet 11 is arranged at the body-facing side of the disposable absorbent hygiene product. Materials suitable for topsheets are commonly known in the art of disposable absorbent hygiene products, and for the purposes of the present application any material commonly known for use a topsheet materials may be used, including, but not limited to non-woven materials and perforated polymeric films.

The topsheet 11 is suitably sufficiently fluid permeable to allow discharged body fluids such as urine to penetrate through the thickness of the topsheet 11. Also, the topsheet 11 is suitably manufactured from a material which is compliant and soft-feeling to the skin of the wearer.

The topsheet 11 may be manufactured from various web materials such as woven and nonwoven webs, perforated films, open cell foams, or combinations or laminates of the above-mentioned materials.

In the context of the present application, a "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding.

The nonwoven materials to be used for the topsheet 11 may for example be made of a spunbond, a spunbond/spunbond composite or a spunbond/meltblown composite, such as a SMS (spunbond/meltblown/spunbond), SSMS, SSMMS, SMMS, nonwoven material of polypropylene or bicomponent fibers of polypropylene and polyethylene, or of a combination of such materials. The topsheet 11 may also have elastic properties.

The topsheet 11 may be hydrophilized in order to improve the tendency for urine to penetrate the topsheet into the underlying structures. Methods for hydrophilizing nonwovens are known to those skilled in the art and include coating the nonwoven material with a hydrophilic coating, such as by applying a surfactant coating; by applying a hydrophilic monomer composition and a radical polymerization initiator onto the nonwoven followed by initiating a polymerization reaction on the nonwoven; by applying a coating of hydrophilic nanoparticles; or by treating the nonwoven surface with a high energy treatment (corona, plasma).

A surfactant coating may be obtained for example by applying a surfactant composition to the non-woven material by any suitable means including spraying, slot coating, kiss roll coating and/or soaking the material in a bath containing the surfactant. The hydrophilization treatment may be performed in-line during assembly of the absorbent article, or may performed separately and the topsheet may then delivered as ready-to-use rolls to the disposable absorbent hygiene product manufacturing plant.

The surfactant coating may be applied to the full width of the topsheet material, or may be limited to a centrally located zone, for example such as to provide a topsheet material with the desired hydrophilicity in the area where it is expected to be directly subjected to body liquid discharges, while the areas laterally outside the hydrophilized zone may remain hydrophobic.

Surfactants used for the hydrophilization of the nonwoven may be any known surfactant suitable for use in hygienic applications, as is generally known in the art. Suitable surface-active agents may include any cationic surfactant, anionic surfactant, nonionic surfactant, zwitterionic surfactant, surfactant of amine oxide type, and silicone based surfactant suitable for use in hygienic applications and should lower the contact angle between the topsheet and urine. Suitable surfactants also provide a relatively long-lasting hydrophilization effect to the non-woven, i.e. they are not readily washed away from the nonwoven, but remains to large extent also after contact with an aqueous liquid, such as urine.

Examples on suitable surface-active agents are; Silastol® PHP26, Silastol® PHP 28, Silastol® 163, Silastol® PHP 207 (products of Schill & Seilacher GmbH of Germany), Stantex® S 6327 (products of Cognis, Pulcra Chemicals of Germany), Duron™ OS 1547, Duron™ OF 4012 (products of CHT/BEZEMA of Germany), Nuwet® 237 and Nuwet® 550 (products of Momentive Performance Materials of New York).

The topsheet material may have a basis weight of from 8 to 20 g/m², such as from 12 to 17 g/m². However, the application is not limited to topsheet materials having this basis weight only.

The topsheet material may have a strikethrough time of at most 7, such as from 1 to 7, for example from 2 to 6 seconds, as measured according to the method NWSP (Nonwoven Standard Procedure) 070.3.R0 (15).

An exemplary topsheet is hydrophilically treated polypropylene spunbond or spunbond-meltblown-spunbond nonwoven having a basis weight of from 8 to 20 g/m².

Topsheet materials suitable for use in a product according to the present application are commercially available for example from Fitesa (Gravitai, Brazil) and Berry Global (Indiana, USA).

Backsheet

A backsheet 12 is arranged at the garment facing side of the disposable absorbent hygiene product. Materials suitable as backsheets are commonly known in the art of disposable absorbent hygiene products. The backsheet 12 prevents the exudates absorbed by the absorbent assembly from soiling other external articles that may contact the disposable absorbent hygiene product, such as bedsheets and undergarments. The backsheet 12 is substantially impermeable to liquids, such as urine, in one embodiment.

The backsheet may be substantially liquid impermeable but breathable, i.e. gas permeable, implying that air and other gases may pass through the backsheet 12, while being substantially impermeable to liquids.

For the purposes of the present application, any material commonly known for use as backsheet materials may be included in the backsheet, including but not limited to polymeric films, for example films of polyethylene, polypropylene or copolymers of polyethylene or polypropylene, hydrophobized nonwoven materials, fluid impermeable foams and fluid impermeable laminates.

The backsheet may comprise one or more layers of material. For example, the backsheet may be a laminate of a liquid impermeably polymeric film towards the absorbent assembly and nonwoven towards the garment side, to provide a textile, soft feeling to the outer surface of the disposable absorbent hygiene product.

Absorbent Assembly

An absorbent assembly 13 is arranged between the topsheet 11 and the backsheet 12. It is here to be noted that an absorbent assembly 13 per se, suitable for use in a disposable absorbent hygiene product, constitutes a separate embodiment of the present application.

The absorbent assembly 13 defines a longitudinal direction from a front end to a back end, and a transversal direction perpendicular to the longitudinal direction. In the disposable absorbent hygiene product, the absorbent assembly is aligned such that the longitudinal direction of the assembly is parallel to the longitudinal direction of the disposable absorbent hygiene product, with the front end of the absorbent assembly towards the front end of the disposable absorbent hygiene product and with the back end of the assembly towards the back edge of the disposable absorbent hygiene product.

The absorbent assembly 13 has a longitudinal length $L_{abs}$ of from 500 to 1000 mm, such as from 550 to 750 mm, for example from 570 to 700 mm, and a transversal width $W_{abs}$ of from 200 to 450 mm, such as from 220 to 350 mm, for example from 230 to 300 mm.

In the context of the present application, a longitudinal length is to be understood as the longest length of a specified part or sub part in the longitudinal direction. Analogously, a transversal width is to be understood as the widest width of a specified part or sub part in the transversal direction.

For the purposes of the present application, and unless otherwise explicitly mentioned, lengths, widths and other dimensions of a disposable absorbent hygiene product are measured with the disposable absorbent hygiene product in a relaxed flattened-out state on a flat surface with any contracting elastics being deactivated.

The absorbent assembly is divided by two transversally extending, longitudinally spaced apart imaginary lines T1, T2, into (i) a front region $R_f$ positioned towards the front edge having a longitudinal length of from 10 to 40, such as from 15 to 30, for example from 17 to 25% of the absorbent assembly longitudinal length, (ii) a back region $R_b$ positioned towards the back edge having a longitudinal length of from 10 to 40, such as from 15 to 30, for example from 17 to 25% of the absorbent assembly longitudinal length, and (iii) a central region $R_c$ between said front region and said back region. For avoidance of doubt the front, central and back regions $R_f$, $R_c$, $R_b$, are non-overlapping, and together constitute the whole absorbent assembly 13.

The planar surface area of the central region $R_c$ is significantly smaller than the planar surface area of the total absorbent assembly. For example, the planar surface area of the central region $R_c$ may be at most 75, at most 60, at most 40, or at most 30% of the planar surface area of the total absorbent assembly.

As used herein, the term "planar surface area" of the absorbent assembly or a portion thereof corresponds to the surface area of a flat surface covered by (hidden behind) the absorbent assembly or the portion thereof when the product is placed on the flat surface in a flattened out state with any elastics removed or deactivated.

In the front region $R_f$ and back region $R_b$, the absorbent assembly comprises a mixture of cellulosic fibers and optionally super absorbent polymers, with a super absorbent polymer concentration of from 0 to 30, such as from 5 to 20, for example from 8 to 15 weight %, based on the total weight of cellulosic fibers and super absorbent articles, and a cellulosic fiber basis weight of from 50 to 200, such as from 70 to 170, for example from 100 to 150 g/m².

It may be advantageous that the in the front and back regions, the absorbent assembly comprises super absorbent polymer, such as in a concentration of at least 5%, such as from 5 to 20, for example from 8 to 15 weight %, in order to provide an absorbent assembly and a disposable absorbent hygiene product having an advantageous balance between good liquid handling and material usage.

The mixture of cellulosic fibers and super absorbent polymer may be evenly distributed in the front and the back region of the absorbent assembly, i.e. the cellulosic fiber basis weight and the super absorbent polymer concentration is essentially consistent over the front and back regions respectively. An evenly distributed mixture of cellulosic fibers and super absorbent polymer in the front and back region allows for these regions to provide an essentially continuous layer of material without any unintentional openings/material discontinuities. Unintentional openings or material discontinuities may impair the liquid handling properties and could also lower a user's confidence in the product's performance.

In the front and the back region of the absorbent assembly, the cellulosic fibers optionally mixed with super absorbent polymer may have a basis weight coefficient of variation of at most 20%, preferably at most 15%, more preferably at most 10%, even more preferably at most 5%, as measured according to the method for measuring basis weight evenness provided in this application.

In the front and the back region of the absorbent assembly, and when the super absorbent polymer concentration in these regions is above 5%, the mixture of cellulosic fibers and super absorbent polymer may have a retention capacity, calculated as g/g absorbency, with a coefficient of variation of at most 20%, preferably at most 15%, more preferably at most 10%, even more preferably at most 5%, as measured according to the method for measuring retention capacity evenness provided in this application.

In the front and the back region of the absorbent assembly, and when the super absorbent polymer concentration in these regions is above 5%, the mixture of cellulosic fibers and super absorbent polymer may have a retention capacity, calculated as $g/10\ cm^2$ absorbency, with a coefficient of variation of at most 30%, preferably at most 25%, more preferably at most 20%, even more preferably at most 15%, most preferably at most 10%, as measured according to the method for measuring retention capacity evenness provided in this application.

Further, the central region $R_c$ provides from 70 to 100%, such as from 75 to 95%, for example from 80 to 90% of the total absorption retention capacity of the absorbent assembly, according to the method for measuring absorption retention capacity as provided in this application.

The retention capacity/planar surface area of the central region $R_c$, i.e. the retention capacity of the central region divided by the planar surface area of the central region, may be significantly higher, such as at least 2 times, at least 3 times, at least 4 times or at least 5 times than the retention capacity/planar surface area of the front region $R_f$ and the back region $R_b$, respectively. The retention capacity/planar surface area of the front region $R_f$ and of the back region $R_b$ may be essentially equal, or may differ by less than 20%.

The total absorption capacity of the product, as measured according to the Rothwell method, ISO 11948, may be at least 1000 ml, such as from 1000 to 3000 ml.

The longitudinal length of the front region $R_f$ and the back region $R_b$ may be equal or different. For example, the longitudinal length of the front region $R_f$ may be from 70 to 130%, such as 80 to 120%, or 90 to 110% of the longitudinal length of the back region $R_b$, to allow for a tailored positioning of the central region, where the major part of the retention capacity resides, depending on the intended user.

Figure 2:
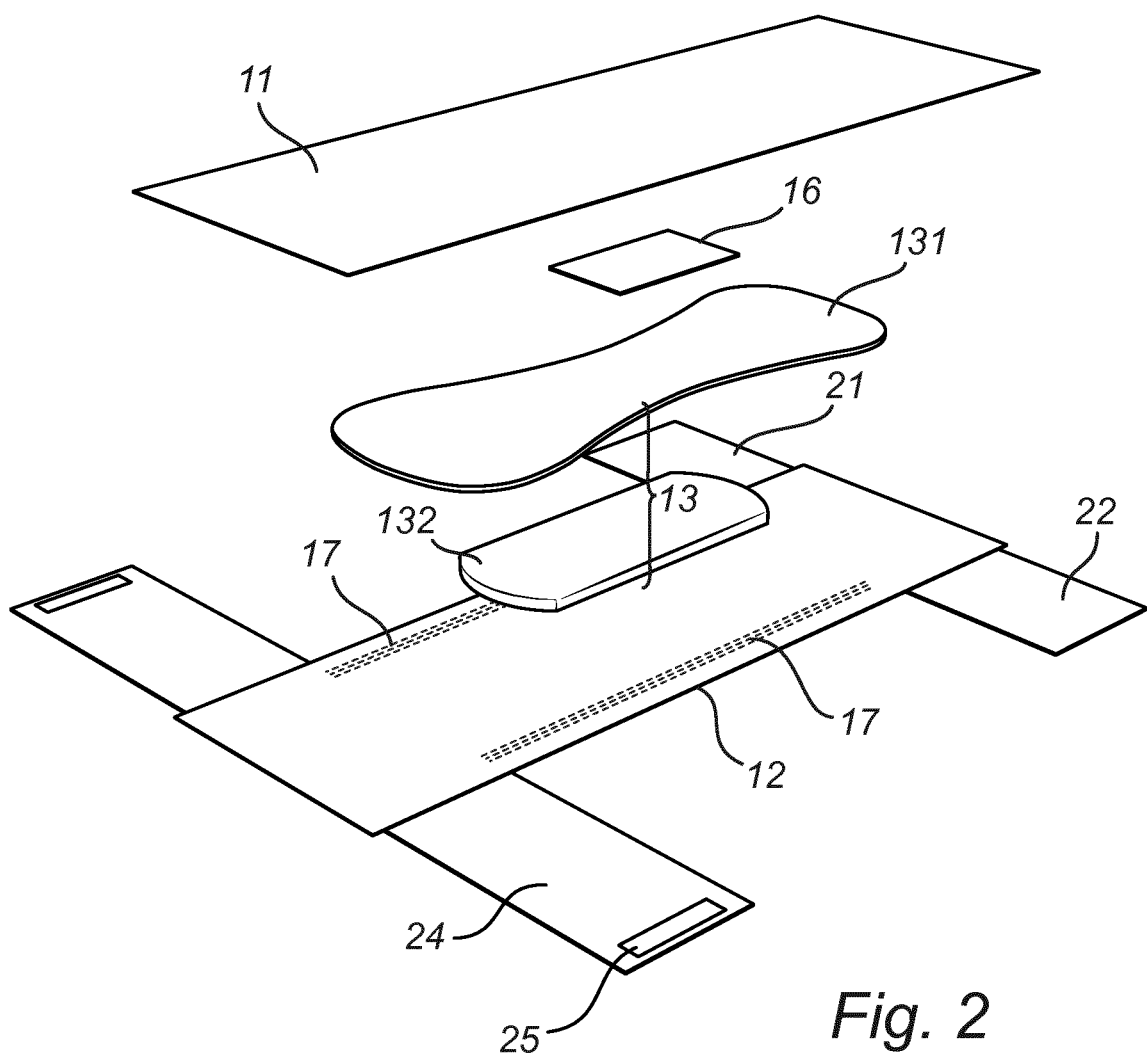
FIG. 2 is an exploded view of the disposable absorbent hygiene product of FIG. 1.

As illustrated in FIGS. 1 and 2, the absorbent assembly 13 comprises two absorbent cores, a first absorbent core 131 and a second absorbent core 132 in a stacked relationship, i.e. placed on top of each other such that both the longitudinal ends of the second absorbent core are between, longitudinally inboard of, the longitudinal ends of the first absorbent core. An absorbent assembly based on two absorbent cores in stacked relationship provides an advantageous design for a disposable absorbent hygiene product according to the present application.

First (Big) Core

The first absorbent core 131 comprises cellulosic fibers optionally mixed with super absorbent polymers, with a super absorbent polymer concentration of from 0 to 30, such as from 5 to 20, for example from 8 to 15 weight %, based on the total weight of cellulosic fibers and super absorbent polymer, and a cellulosic fiber basis weight of from 50 to 200, such as from 70 to 170, for example from 100 to 150 $g/m^2$. The first absorbent core extends over the full longitudinal length of the absorbent assembly.

Second (Small) Core

The second absorbent core 132 is positioned in said central region, and the longitudinal extension of the second absorbent core 132 coincides with the longitudinal extension of the central region $R_c$, such that the transversal lines $T_1$, $T_2$ coincide with the longitudinally outermost ends of the second absorbent core 132.

The second absorbent core 132 comprises a mixture of cellulosic fibers and superabsorbent particles, with a super absorbent polymer concentration of from 20 to 70, such as from 25 to 50, for example from 30 to 40 wt % and having a cellulosic fiber basis weight of from 250 to 500, such as from 300 to 450 $g/m^2$.

The planar surface area of the second absorbent core 132 is smaller than that of the first absorbent core, for example, it may be less than 75%, such as less than 60% or less than 50%, for example from 40 to 75% of that of the first absorbent core 131.

In the embodiment illustrated in FIG. 1, the second absorbent core 132 is on the garment facing side of the first absorbent core 131, positioned between the first absorbent core 131 and the backsheet 12. In alternative embodiments, the second absorbent core 132 may be on the body facing side of the first absorbent core 131, positioned between the first absorbent core 131 and the topsheet 11.

In a disposable absorbent hygiene product in according to the present application where the second absorbent core is positioned between the first absorbent core and the backsheet, the first absorbent core may partly act as a transfer layer for directing fluid away from the topsheet and into the second absorbent core, where the major portion of the liquid retention capacity is concentrated, thereby contributing to a good liquid handling in the product.

The first absorbent core 131 and the second absorbent core 132 may be in direct contact with each other, meaning that there is no additional material layer, such as a tissue or non-woven core wrap layer, between the two cores.

Core Forming

A core consisting of cellulosic fibers and super absorbent polymer may in general be produced by different methods known to the person skilled in the art, such as by milling, comminuting, cellulosic material into cellulosic fibers, mixing the fibers with super absorbent polymer, depositing the mixture onto a core forming drum and debulking the core before transferring the drum to a substrate, such as a web material of the disposable absorbent hygiene product, for example to a topsheet material web or to a backsheet material web. Such cores are commonly known as airfelt-based cores. In the absorbent assembly of the present application, at least the front region $R_f$ and the back region $R_b$, such as the first absorbent core 131 and optionally the second absorbent core 132 may be airfelt-based, i.e. based on comminuted cellulosic fibers, optionally mixed with super absorbent polymers.

In a core with a low cellulosic fiber basis weight, excessive flocculation may lead to undesired holes/openings in the core layer that will be detrimental to product performance and also to the visual appearance and to the user's tendency to trust the product, thereby the willingness to use the product.

A high basis weight evenness, i.e. low basis weight coefficient of variation, may be achieved by placing the mill very close to the core forming drum such as to prevent flocculation of the milled fibers in the pathway from the mill to the core forming drum. For a good distribution of the super absorbent polymer, it may be advantageous to add the SAP close to the mill for achieving a good mixture with the milled fibers prior to deposition on the core forming drum.

Cellulosic materials that can be milled, comminuted, and then used in absorbent cores according to the present application are well known in the art and include wood pulp, cotton, flax and peat moss. Wood pulp is preferred in one embodiment. Pulps can be obtained from mechanical or chemi-mechanical, sulfite, kraft, pulping reject materials, organic solvent pulps, etc. Both softwood and hardwood species are useful. Softwood pulps are preferred in one embodiment. It is not necessary to treat cellulosic fibers with chemical debonding agents, cross-linking agents and the like for use in the present material. Some portion of the pulp may be chemically treated for improved flexibility of the product. The flexibility of the material may also be improved by mechanically working the material or tenderizing the material.

Core Positioning

The absorbent assembly may be longitudinally centralized within the main part, i.e. the longitudinal distance $D_f$ from the front edge of the absorbent assembly 13 to the front edge of the main part 10 is equal to the longitudinal distance $D_b$ from the back edge of the absorbent assembly 13 to the back edge of the main part 10, or $D_b$ may be different from $D_f$ to tailor the position of absorption retention capacity within the product. For example, the distances $D_f$ and $D_b$ may independently be from 100 to 300 mm.

As illustrated in FIG. 1, the outer contour of the absorbent assembly may be hourglass shaped, such that the where the width of the central region $R_c$ is narrower than the width of the front region $R_f$ and the back region $R_b$, respectively, where the width of the back region and the front region may be equal or different. For example, the back region may be wider than the front region.

In alternative embodiments, the outer contour of the absorbent assembly may take different shapes, such as rectangular or oblong.

SAP

Superabsorbent polymers are well-known in the field of absorbent products and is used to help improve the absorbent properties of such products. Superabsorbent polymers are constituted by water-swellable and water-insoluble polymers that are capable of absorbing large quantities of fluid upon formation of a hydrogel, such as capable of absorbing at least 5 times their weight of an aqueous 0.9% saline solution as measured according to the method NSWP 241.0.R2 (15). The superabsorbent polymer polymers for use in accordance with the present application may be inorganic or organic crosslinked hydrophilic polymers, such as polyvinyl alcohols, polyethylene oxides, crosslinked starches, guar gum, xanthan gum, crosslinked polyacrylates, and the like. The polymers may be in the form of powders, granules, microparticles, films, foams and fibers, for example. Upon contact with fluids, such super absorbent polymers swell by absorbing the fluids into their structures. In general, super absorbent polymers can quickly absorb fluids insulted into such articles, and can retain such fluids to prevent leakage and help provide a dry feel even after fluid insult.

The type of super absorbent polymer used in an absorbent assembly of the present invention may be the same or may vary within the assembly. For example, super absorbent polymer with a first set of characteristics may be used in the front and back regions of the absorbent assembly, or in the first absorbent core, and super absorbent polymer with a second set of characteristics may be used in the central region of the absorbent assembly, or in the second absorbent core. The characteristics referred to in this section is for example the centrifuge retention capacity (CRC), absorption under load (AUL) and/or the gel layer permeability (GLP).

The first and/or second absorbent core as discussed above may have an even or a profiled distribution of super absorbent polymer along the thickness of the absorbent core, i.e. along a direction from the body-facing to the garment facing side of the absorbent core. For example, the majority, such as at least 50, for example from 70 to 95 wt % of the super absorbent polymer may be positioned in a middle region, thickness-wise, of the absorbent core. The middle portion may for example constitute 50% or less, such as from 30 to 50% of the total thickness of the core, where the middle region is positioned sandwiched between a body-facing region and a garment facing region, each constituting half of the remainder, thickness-wise, of the absorbent core, wherein the garment facing region and the body facing region together contain the remainder of the super absorbent polymer amount. The three regions thickness-wise may be clearly distinguishable and easily separable from each other, or may be integral with each other.

Acquisition Layer

According to the present application, a disposable absorbent hygiene product may comprise an acquisition layer 16 arranged between the topsheet 11 and the absorbent assembly 13.

As illustrated in FIG. 1, such acquisition layer 16 may be arranged sandwiched between the topsheet 11 and the absorbent assembly 13, on top of the central region $R_c$ of the absorbent assembly. The acquisition layer may be at least partially within, such as wholly within the central region R. For example, the contour of the acquisition layer 16 may be fully within the contour of the second absorbent core 132, when viewed from the top with the product in a flattened-out state on a planar surface.

While an absorbent assembly of the present application is intended to receive and hold large amounts of exudates, such as urine, it may be advantageous to include an acquisition layer between the topsheet and the absorbent assembly provide for interim acquisition of large amounts of liquid, as well as providing a layer for the distribution of liquid away from the immediate place of impact.

Materials suitable as acquisition layers, also referred to in the art as transfer layer, or ADL (acquisition and distribution layer), are commonly known in the art of disposable absorbent hygiene products, and for the purposes of the present application, any material known to the person skilled in the art as being useful as an acquisition layer may be used. An acquisition layer may for example be in the form of an airlaid layer, a spunlace layer, a high-loft, foam or any other type of material layer which may be used in an absorbent article to act as a liquid acquisition and absorption layer. The acquisition layer is suitably adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by pressure and vacuum. The acquisition layer is of an air-through bonded nonwoven of polyester fibers in one embodiment.

The acquisition layer may have a basis weight from 20 to 100, such as from 30 to 80, for example from 40 to 60 g/m2.

The acquisition layer may have a sufficiently high caliper before the article is used, but also maintain a high caliper even in use conditions when the article is subject to external pressure. The acquisition layer may have a caliper from 0.5-3 mm, such as from 0.9 to 2 mm, for example from 1 to 1.5 mm, at a pressure of 0.5 kPa as measured according to the method NWSP 120.6.RO (15), method option A.

One exemplary acquisition material is commercially available from Berry Italy under the tradename B5, and is a through-air bonded nonwoven having a basis weight of 40-60 g/m$^2$ and a caliper of about 1 mm, comprising a mixture of about 50 weight % polyester fibres and the remainder of the fibers being bi-component fibers of polyester.

The acquisition material may comprise a blend of different fibers, such as a blend of two or more types of fibers. Such blend may comprise at least 10, 20, 30, 40, 50, 60, 70, 80, or 90 weight % of a first type and the remaining weight % portion of other types of fiber types of fibers and optionally further components, such as binders, such as latex. The fibers of the acquisition layer may comprise or consist of polyester. For example, the blend may comprise from 40 to 60 weight % of a first type of fiber, and from 30 to 60 weight % of a second type of fiber. The acquisition layer may optionally comprise up to 30 weight %, more preferably up to 20 weight % of additional components.

The first type of fiber may be a fiber exhibiting a spiral-crimp, preferably from polyester in one embodiment. As used herein, a spiral-crimp is any three-dimensional crimp, for example one wherein the fibers substantially assume a helical shape. The spiral-crimp fiber may consist of or comprise hollow fibers, i.e. a fiber whose cross-sectional area is hollow, such as 10 to 30%, for example 15 to 20% of the cross sectional area is hollow.

The second fiber may comprise or consist of a polyester bi-component fiber, such as a core-sheath fiber with a lower melting temperature material in the sheath and a higher melting temperature material in the core.

In the blend, the second type of fibers may be thinner than the first type of fibers. The second type of fibers may have 3-9, such as 5-8, for example 6-7 dtex. The first type of fibers may have 8-12, such as 9-10 dtex. The first type of fibers and the second type of fibers may be of different length, or of the same length. The fibers may have an average length from 20 to 70 mm, such as from 30 to 50 mm.

Acquisition materials of through-air bonded nonwovens comprising spiral crimp fibers of polyester and polyester bi-component fibers are generally disclosed in International Patent Application Publication No. WO99/00098 to SCA Hygiene Products AB, the contents of which is included herein by reference.

Without wishing to be bound by theory, it is further believed that the spiral crimping of fibers is very beneficial for their liquid acquisition and distribution behavior. It is assumed that the spiral crimp increases the void space in an acquisition member formed by such fibers. Often, an absorbent article, when being worn, is exposed to a certain pressure exerted by the wearer, which potentially decreases the void space in the acquisition member. Having good permeability and sufficient void space available are desirable for good liquid distribution and transport. It is further believed that the spiral-crimped fibers as described above are very suitable to maintain sufficient void volume even when an acquisition member is exposed to pressure. In addition, spiral-crimped fibers believed to provide for good permeability as for a given fiber dtex value, and a hollow fiber cross-section allows for a larger outer diameter of the fiber as compared to a compact cross-section. The outer diameter of a fiber appears to determine the permeability behavior of an acquisition member formed by such fibers.

Additional Components

Further components commonly employed in disposable absorbent hygiene products but not illustrated in the figures of the present application may be employed in a disposable absorbent hygiene product according to the present application.

For example, raised elastic members, commonly known as standing gathers, may be attached to the topsheet.

A wetness indicator, for example a material that changes its color upon contact with urine, may be included in the disposable absorbent hygiene product, such as disposed between the absorbent assembly and the backsheet and visible through the backsheet, such as to indicate whether a wetting event has taken place.

Moreover, when the disposable absorbent hygiene product is an incontinence pad, a fastening means, such as a strip of pressure sensitive adhesive, may be disposed on the garment facing side of the backsheet to provide secure placement of the pad in the underwear.

Methods

Method for Measuring Basis Weight Evenness

For the evaluation, take five adjacent diapers from one and the same consumer package, or take five consecutively produced diapers from production.

Unfold the diapers if folded, and lay bare for 48 hours in a stable laboratory environment set to 23° C. and 50% relative humidity. Testing is performed in this same environment.

Figure 3:
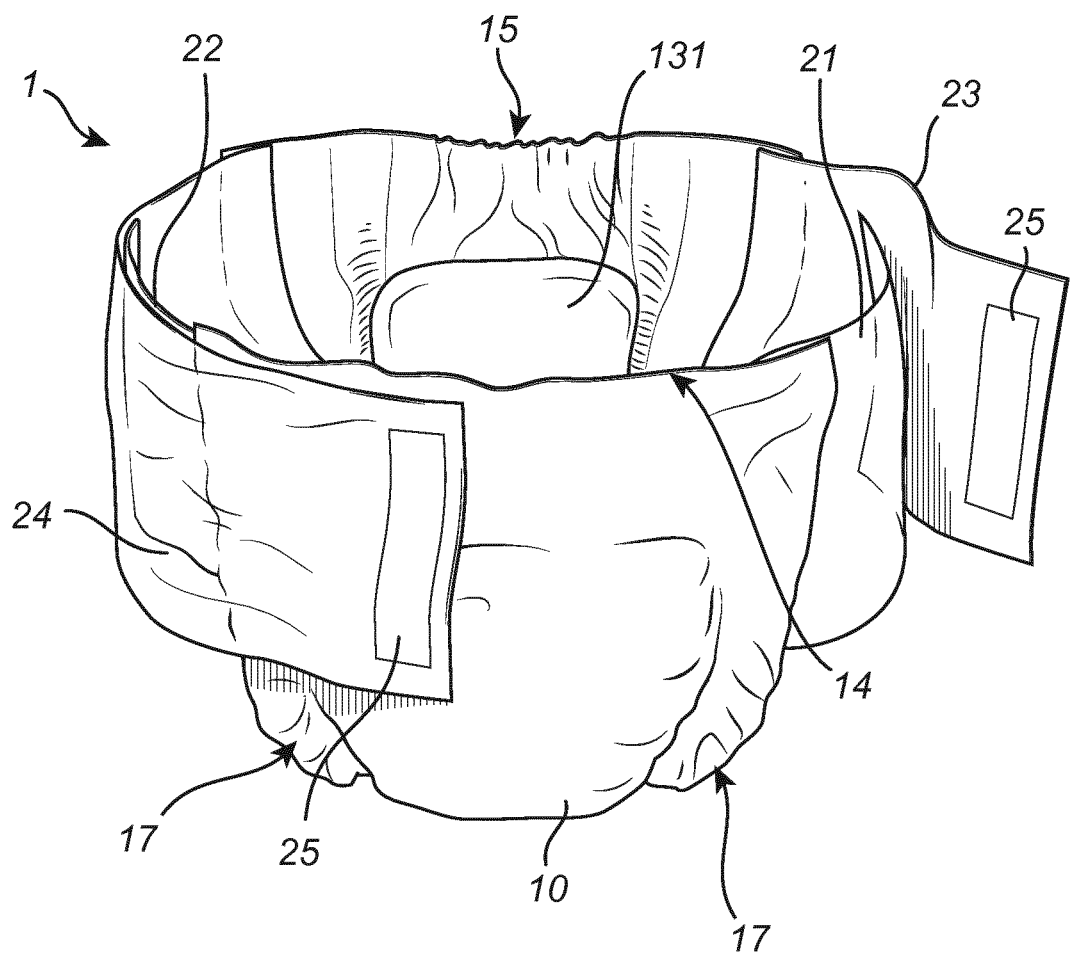
FIG. 3 is a perspective view of the disposable absorbent hygiene product of FIG. 1 in a closed state.

Remove or neutralize all elastic elements in the diaper, and place the diaper smooth and flat. Samples for evenness evaluation are then punched out from the diaper. The punching tool has outer dimensions of 50×120 mm, with cutting cross bars every 20 mm. The tool thus cuts 6 adjacent samples, each sample measuring 50×20 mm (10 cm$^2$). Two sets of 6 individual samples (12 samples in all) are cut from each diaper. Referring to FIG. 3, one set of six samples is taken from the front region ($R_f$), and the other from the back region ($R_b$). The punching tool should be placed immediately outside the central region ($R_c$). The tool's length dimension coincides with the diaper's transverse direction. The punching tool should be centered on the diaper's longitudinal centerline (C).

Determine the weight (to the nearest milligram) of each 50×20 mm core sample. For this purpose, any additional layers (such as the topsheet or the backsheet) first should be subtracted. Take care so that no superabsorbent or significant amounts of fibers are lost when laying bare the core. Alternatively, the punched sample can be weighed as is. The basis weight of the additional layers then should be known beforehand (from the material specification or a separate determination), so that their weight can be subtracted from the samples.

Calculate the basis weight (g/m$^2$) for each sample from the large core:

(Sample weight (g))/(Sample area (0.001 m$^2$))

Calculate the (arithmetic) mean basis weight (g/m$^2$) for the series of 60 samples, and then calculate the standard deviation for the series:

$$s = \sqrt{\frac{\sum_{i=1}^{N}(x_i - \bar{x})^2}{N-1}}$$

where x is the basis weight of the individual sample, $\bar{x}$ is the arithmetic mean, and N is the number of samples (count 60).

Finally calculate the coefficient of variation (CV) by dividing the standard deviation by the mean. Express the ratio in percent (%).

Method for Measuring Evenness of Retention Capacity

This test evaluates the evenness of the retention capacity in the front and back regions of the absorbent assembly, an indicates the distribution of superabsorbent polymer. For this purpose, make use of the same 60 samples that were used in the Basis Weight Evenness test (described above).

As a conventional superabsorbent polymer absorbs way more than cellulosic fibers, a suitable test method has been found in the CRC-test (Centrifuge Retention Capacity). The method is well known in the industry, and is available from EDANA or INDA under the full name Standard Procedure: NWSP 241.0.R2 (15), entitled "Polyacrylate Superabsorbent Powders—Determination of the Fluid Retention Capacity in Saline Solution by Gravimetric Measurement Following Centrifugation".

A sample is placed in a sealable nonwoven bag, and the sample is then immersed in a 0.9% NaCl solution for 30 minutes. The sample is thereafter centrifugated in a 250 g-force to remove interstitial fluid, after which g/g absorbency and g/sample absorbency, i.e. g/10cm$^2$ absorbency is determined.

g/g absorbency=(final sample weight−initial sample weight)/initial sample weight g/10cm$^2$ absorbency=final sample weight−initial sample weight The skilled person can easily adopt the test to a 20×50 mm excision from the core. However, note that larger nonwoven bags should be used to accommodate the larger core samples. Only the core components (conventionally the cellulose pulp and the superabsorbent) are included in the g/g absorbency calculation. Any additional layers (such as topsheet or backsheet) only can be included with the core sample if they are substantially non-absorbent (such as polyolefin or polyester films or fibers), and their dry weight should then be subtracted in all sample weight determinations. Additional layers containing absorbent material (such as viscose or cotton fibers) should be removed before testing.

Calculate Coefficient of Variation (CV) for the g/g absorbency and g/10 cm$^2$ in the series of 60 samples from the core. The calculation principle is the same as in the Basis Weight Evenness test Total Retention Capacity of the Absorbent Assembly Retention capacity of the absorbent assembly can easily be evaluated along the principles of the CRC-test (Centrifuge Retention Capacity). This method is well known in the industry, and is available from EDANA or INDA under the full name Standard Procedure: NWSP 241.0.R2 (15). Polyacrylate Superabsorbent Powders—Determination of the Fluid Retention Capacity in Saline Solution by Gravimetric Measurement Following Centrifugation. However, the test is designed for small samples, and some modifications are performed for evaluating a whole absorbent assembly as described below.

Diapers for testing are removed from their package, unfolded, and laid bare for 48 hours in a stable laboratory environment set to 23° C. and 50% relative humidity. Testing is performed in this same environment.

Isolate the absorbent assembly, using a pair of scissors or a scalpel. Take care so that no superabsorbent particles escape. Weigh the assembly, and then place it in a pouch made of a nonwoven or woven web (suitable web properties are described in the standard NWSP 241.0.R2). Then seal the pouch using a heat sealer. (In case the absorbent assembly is unpractically big it can of course be split in smaller parts, whose respective absorbencies are then added up.) Submerge the pouch in 3 liters of 0.9% NaCl solution (change solution for each individual sample), and let it absorb for 30 minutes. Then centrifuge the assembly for 3 minutes in a 250 g force. Finally subtract the weight of the dry assembly and the pouch. The amount of saline solution thus retained signifies the total retention capacity of the absorbent assembly.

The test can also be performed on the central region ($R_c$) alone, or other relevant regions. In this case the region is carefully cut loose using a pair of scissors or a scalpel. For comparing the central region ($R_c$) capacity to the capacity of the whole absorbent assembly, use 10 representative diapers for each retention determination, and calculate the ratio (in percent) between the respective arithmetic means.

The embodiments described above are only descriptions of preferred embodiments of the present invention, and are not intended to limit the scope of the present invention. Various variations and modifications can be made to the technical solution of the present invention by those of ordinary skill in the art, without departing from the design and spirit of the present invention. The variations and modifications should all fall within the claimed scope defined by the claims of the present invention.

What is claimed is:

1. A disposable absorbent hygiene product comprising:
   a main part having a body facing surface intended to face a body of a user and a garment facing surface intended to face away from the body of a user,
   the main part comprising a liquid permeable topsheet at the body facing surface, a liquid impermeable backsheet at the garment facing surface, and an absorbent assembly arranged between said topsheet and said backsheet, said main part having a having a front end and a back end and defining a longitudinal direction from said front end towards said back end and defining a transversal direction perpendicular to the longitudinal direction,
   wherein the absorbent assembly includes a first absorbent core and a second absorbent core arranged in a stacked relationship,
   wherein said first absorbent core has a longitudinal length of from 500 to 1000 mm and a transversal width of from 200 to 450 mm and comprises cellulosic fibers mixed with super absorbent particles, having a super absorbent particle concentration of from 0 to 30 wt %, and a cellulosic fiber basis weight of from 50 to 200 g/m$^2$;
wherein said second absorbent core has a longitudinal length of from 20% to 80% of the longitudinal length of said first core and comprises a mixture of cellulosic fibers and super absorbent particles, with a super absorbent particle concentration of from 20 to 70 wt %, and a cellulosic fiber basis weight of from 250 to 500 g/m$^2$;
wherein longitudinal ends of the second core are located between longitudinal ends of the first core; and
wherein said second absorbent core is positioned between said first absorbent core and said backsheet such that the first absorbent core, which defines a longest longitudinal length of the first and second absorbent cores and a smallest super absorbent particle concentration of the first and second absorbent cores, is located closer to the topsheet than the second absorbent core.

2. The product according to claim 1, wherein a planar surface area of said second absorbent core is at most 75% of a planar surface area of said first absorbent core.

3. The product according to claim 1, wherein said absorbent assembly is divided by a first imaginary, transversally extending line coinciding with the front end of the second core and a second imaginary, transversally extending line coinciding with the back end of the second core into a front region towards said front end of the main part, a back region towards said back end of the main part; and a central region between said front region and said back region.

4. The product according to claim 3, wherein said central region provides at least 70% of a total retention capacity of the absorbent assembly.

5. The product according to claim 3, wherein at least one of the front region has a longitudinal length of from 17% to 25% of the longitudinal length of the absorbent assembly and the back region has a longitudinal length of from 17% to 25% of the longitudinal length of the absorbent assembly.

6. The product according to claim 1, wherein said second absorbent core has a transversal width of from 100 to 200 mm.

7. The product according to claim 3, wherein a ratio of a retention capacity to a planar surface area of the central region is at least 2 times a ratio of a retention capacity to a planar surface area of the front region and the back region.

8. The product according to claim 1, wherein said first absorbent core comprises a comminuted cellulosic fibers mixed with super absorbent polymers.

9. The product according to claim 3, wherein said mixture of cellulosic fibers and superabsorbent particles in said front and back regions has a basis weight coefficient of variation of at most 20%.

10. The product according to claim 1, wherein said first absorbent core comprises a mixture of cellulosic fibers and super absorbent particles, with a super absorbent particle concentration of at least 5 weight %.

11. The product according to claim 10, wherein said mixture of cellulosic fibers and super absorbent particles has at least one of a retention capacity, calculated as g/g absorbency with a coefficient of variation of at most 20%, and a retention capacity, calculated as g/10 cm$^2$ absorbency with a coefficient of variance of at most 30%.

12. The product according to claim 1, wherein said first absorbent core is in direct contact with said second absorbent core.

13. The product according to claim 1, having a total absorption capacity of at least 1000 ml.

14. The product according to claim 3, further comprising:
an acquisition layer material sandwiched between said topsheet and said absorbent assembly.

15. The product according to claim 14, wherein said acquisition layer material is wholly positioned within an area of said central region.

16. The product according to claim 3, wherein the product comprises one of an open type diaper, a pant type diaper, a belt type diaper, an incontinence pad and a removable insert.

17. The product according to claim 2,
wherein said absorbent assembly is divided by a first imaginary, transversally extending line coinciding with the front end of the second core and a second imaginary, transversally extending line coinciding with the back end of the second core into a front region towards said front end of the main part, a back region towards said back end of the main part; and a central region between said front region and said back region,
wherein said central region provides at least 70% of a total retention capacity of the absorbent assembly,
wherein at least one of the front region has a longitudinal length of from 17% to 25% of the longitudinal length of the absorbent assembly and the back region has a longitudinal length of from 17% to 25% of the longitudinal length of the absorbent assembly,
wherein said second absorbent core has a transversal width of from 100 to 200 mm,
wherein a ratio of a retention capacity to a planar surface area of the central region is at least 2 times a ratio of a retention capacity to a planar surface area of the front region and the back region,
wherein said first absorbent core comprises a comminuted cellulosic fibers mixed with super absorbent polymers,
wherein said mixture of cellulosic fibers and superabsorbent particles in said front and back regions has a basis weight coefficient of variation of at most 20%,
wherein said first absorbent core comprises a mixture of cellulosic fibers and super absorbent particles, with a super absorbent particle concentration of at least 5 weight %,
wherein said mixture of cellulosic fibers and super absorbent particles has at least one of a retention capacity, calculated as g/g absorbency with a coefficient of variation of at most 20%, and a retention capacity, calculated as g/10 cm$^2$ absorbency with a coefficient of variance of at most 30%,
wherein said first absorbent core is in direct contact with said second absorbent core,
wherein the product has a total absorption capacity of at least 1000 ml,
wherein the product further comprises an acquisition layer material sandwiched between said topsheet and said absorbent assembly,
wherein said acquisition layer material is wholly positioned within an area of said central region, and
wherein the product comprises one of an open type diaper, a pant type diaper, a belt type diaper, an incontinence pad and a removable insert.

\* \* \* \* \*